(12) United States Patent
Smith et al.

(10) Patent No.: US 12,112,840 B2
(45) Date of Patent: *Oct. 8, 2024

(54) IMPORTING STRUCTURED PRESCRIPTION RECORDS FROM A PRESCRIPTION LABEL ON A MEDICATION PACKAGE

(71) Applicant: Walmart Apollo, LLC, Bentonville, AR (US)

(72) Inventors: Walter R. Smith, Seattle, WA (US); Chi-Kai Chien, Los Altos Hills, CA (US); Christian Hagel-Sorensen, Sammamish, WA (US); Frédéric Médous, San Francisco, CA (US); Peyman Oreizy, Seattle, WA (US); Jonathan Schwartz, San Francisco, CA (US); Brittany Staten, San Francisco, CA (US); Paul Teixeira, San Francisco, CA (US)

(73) Assignee: WALMART APOLLO, LLC, Bentonville, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/231,150

(22) Filed: Aug. 7, 2023

(65) Prior Publication Data

US 2024/0029845 A1     Jan. 25, 2024

Related U.S. Application Data

(63) Continuation of application No. 14/656,691, filed on Mar. 12, 2015, now Pat. No. 11,721,414.

(51) Int. Cl.
*G16H 10/60* (2018.01)
*G06V 30/142* (2022.01)
(Continued)

(52) U.S. Cl.
CPC ............ *G16H 10/60* (2018.01); *G06V 30/142* (2022.01); *G16H 20/10* (2018.01); *G16H 30/20* (2018.01);
(Continued)

(58) Field of Classification Search
CPC ........ G16H 10/60; G16H 20/10; G16H 30/20; G06V 30/142; G06V 30/10; G06V 30/141;
(Continued)

(56) References Cited

U.S. PATENT DOCUMENTS

| | | | |
|---|---|---|---|
| 8,712,163 B1* | 4/2014 | Osheroff | G06F 18/00 424/467 |
| 2008/0306787 A1* | 12/2008 | Hamilton | G06Q 10/0639 705/7.38 |
| 2009/0196485 A1* | 8/2009 | Mueller | G06V 10/993 382/137 |
| 2010/0303363 A1 | 12/2010 | Fedorovskaya | |

(Continued)

*Primary Examiner* — Chad A Newton
(74) *Attorney, Agent, or Firm* — BRYAN CAVE LEIGHTON PAISNER LLP

(57) ABSTRACT

A system comprising one or more processors, and one or more non-transitory computer-readable media storing computing instructions that, when executed on the one or more processors, cause the one or more processors to perform operations comprising: displaying, one or more instructions on a user interface of a mobile device to instruct a user to capture each respective image of a prescription label; determining, using contrast, a location of each respective image in the set of images that is associated with the respective different portions of the prescription label on the medication package; reconstructing each of the respective different portions of the prescription label on the medication package as a flattened reconstruction of the respective different portions of the prescription label; and providing for display on the user interface a reconstructed prescription label. Other embodiments are disclosed herein.

20 Claims, 11 Drawing Sheets

(51) Int. Cl.
*G16H 20/10* (2018.01)
*G16H 30/20* (2018.01)
*G16Z 99/00* (2019.01)
*G06V 30/10* (2022.01)
*G06V 30/14* (2022.01)
*H04N 23/60* (2023.01)

(52) U.S. Cl.
CPC .............. *G16Z 99/00* (2019.02); *G06V 30/10* (2022.01); *G06V 30/141* (2022.01); *H04N 23/64* (2023.01)

(58) Field of Classification Search
CPC .... G16Z 99/00; H04N 23/64; H04N 5/23222; G06F 19/3456; G06F 19/00; G06K 9/228; G06K 2209/01; G06K 2009/2045
See application file for complete search history.

(56) References Cited

U.S. PATENT DOCUMENTS

| | | |
|---|---|---|
| 2011/0085085 A1 | 4/2011 | Yamashita |
| 2011/0202366 A1 | 8/2011 | Akers et al. |
| 2011/0246220 A1 | 10/2011 | Albert |
| 2013/0141524 A1* | 6/2013 | Karunamuni ......... G06T 3/4038 348/38 |
| 2013/0208084 A1* | 8/2013 | Brunner ............... H04N 23/698 348/36 |
| 2013/0275849 A1 | 10/2013 | King |
| 2014/0188502 A1 | 7/2014 | Defrank |
| 2014/0281871 A1 | 9/2014 | Brunner et al. |
| 2014/0355881 A1* | 12/2014 | Bhardwaj ............. G06T 7/0002 382/173 |
| 2015/0324848 A1 | 11/2015 | Graham et al. |
| 2016/0176358 A1 | 6/2016 | Raghu |
| 2018/0199065 A1* | 7/2018 | Adams ................. H04N 19/503 |
| 2018/0366218 A1 | 12/2018 | Smith et al. |

* cited by examiner

IMPORTING STRUCTURED PRESCRIPTION RECORDS FROM A PRESCRIPTION LABEL ON A MEDICATION PACKAGE

CROSS-REFERENCE TO RELATED APPLICATIONS

The present application is a Continuation Application of U.S. patent application Ser. No. 14/656,691, filed on Mar. 12, 2015, which is herewith incorporated by reference in its entirety.

BACKGROUND

This invention relates generally to medication management and more specifically to automated importing of prescription records.

Health care technology becomes ever more effective as we discover new diagnostic techniques and treatments, and make existing treatments cheaper and more common. Many diseases that once required hospital stays are now treatable as chronic conditions, giving patients longer, higher-quality lives. However, as health care processes move out of the professional environment, their day-to-day management increasingly falls on the patients and their families, who are ill-equipped to cope.

Medication management is a particularly difficult aspect of health care. As more conditions become treatable with prescription drugs in pill form, patients are being given more complex medication schedules. Nowadays, it is not rare for patients to be expected to implement a daily regimen of ten or more different medications on a strict schedule.

Aside from daily schedule, the medication list itself causes difficulties. Patients are often being treated by several independent clinics and physicians that do not share health records. This means that when a patient sees a new physician, the patient himself is the only source of knowledge about his medical history and current medication list. The task of maintaining that information falls to the patient because no single clinic or pharmacy can be sure it has access to all the information.

Pharmacists have a responsibility to check a patient's entire medication list for possible mistakes or dangerous drug interactions. However, if a patient goes to multiple pharmacists, none of them have the complete list. Again, only the patient has all the information needed to make a complete check.

Various services have arisen to help patients with these management tasks. For example, there are websites that let patients look up drug interactions themselves, and mobile phones applications that can be programmed to issue reminders to take pills at the right times. All of these services have the weakness that, to operate effectively, they require an accurate list of medications, which is difficult to obtain.

Many services rely on patients to enter their medication lists manually. Accurate transcription of a medication list is difficult for the layperson due to the technical details of instructions and dosage, and the hard-to-spell and easily-confused names of drugs. As a result, these services suffer from lack of accuracy and lack of use.

A more accurate method would be to derive the list from the original prescription records held by the patients' pharmacies. However, such records are typically kept in proprietary systems that may be inaccessible to patients, expensive or cumbersome to access, or unavailable in a format usable by a patient's chosen service.

Therefore, there is a need for a method that allows a service to import accurate prescription records for a patient, without manual entry by the patient, and without access to the proprietary systems in which those records are stored.

SUMMARY

The present invention involves a method and system for deriving computerized prescription records from the information that is printed on a label of a medication package (e.g., pill bottle, medication box, etc.) provided to patients. The system captures portions of a label on a package in a set of images, reconstructs the label based on the set of images, identifies text in the label, determines associations of identified text and types of information, and stores the set of images, the reconstructed label, the identified text in the label, and the determined associations as, for example, a batch in a review queue. During a review process, the batch is reviewed and a structured prescription record is determined for the batch, which is further used by the system and user of the system associated with the batch to provide various features to the user.

Thus, the user can easily and conveniently capture his prescription information without having to manually input it. The system determines the prescription information (e.g., medication name, patient name, physician information, pharmacy, instructions for taking medication, quantity, refills, etc.) based simply on one or more images taken by the user of the medication label and stores this information for the user. From this information can flow various features that are automatically set up by the system for the user based on the captured prescription information. For example, the system can automatically set up a medication list for the user, can prepare refill reminders, can create reminders to the user throughout the day to take the medication, can provide dosage tracking information (which can also be shared with family members that might want to confirm that the right doses were taken at the right time), among a variety of other features. The can all be triggered by and conveniently flow from the images taken by the user of the label such that the user does not have to bother with inputting additional information or setting up all of these features and reminders.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Various embodiments can include a system. A system including one or more processors and one or more non-transitory computer-readable storage devices storing computing instructions, when executed on the one or more processors, cause the one or more processors to perform certain acts. The acts can include displaying, by a medication management system, one or more instructions on a user interface of a mobile device to instruct a user to capture each respective image in a set of images of respective different portions of a prescription label on a medication package. The acts also can include determining, using contrast, a location of each respective image in the set of images that is associated with the respective different portions of the prescription label on the medication package. The acts further can include reconstructing, using the set of images and one or more transform functions, each of the respective different portions of the prescription label on the medication package as a flattened reconstruction of the respective different portions of the prescription label. The acts additionally can include providing, by the medication management system, for display on the user interface a reconstructed prescription label based at least in part on the flattened reconstruction of the respective different portions of the prescription label.

Figure 1:
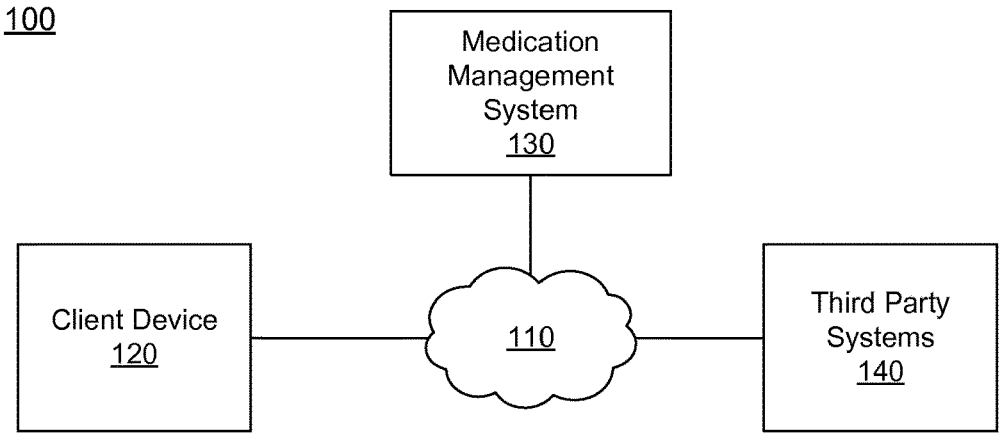
FIG. 1 is a block diagram of a system environment in which a medication management system operates, in accordance with an embodiment.

A number of embodiments can include a method. The method can be implemented via execution of computing instructions configured to run on one or more processors and stored at non-transitory computer-readable media. The method can include displaying, by a medication management system, one or more instructions on a user interface of a mobile device to instruct a user to capture each respective image in a set of images of respective different portions of a prescription label on a medication package. The method also can include determining, using contrast, a location of each respective image in the set of images that is associated with the respective different portions of the prescription label on the medication package. The method further can include reconstructing, using the set of images and one or more transform functions, each of the respective different portions of the prescription label on the medication package as a flattened reconstruction of the respective different portions of the prescription label. The method additionally can include providing, by the medication management system, for display on the user interface a reconstructed prescription label based at least in part on the flattened reconstruction of the respective different portions of the prescription label System Architecture FIG. 1 is a block diagram of a system environment 100 for a medication management system 130. The system environment 100 shown by FIG. 1 comprises a network 110, one or more client devices 120, the medication management system 130, and one or more third party systems 140. In alternative configurations, different and/or additional components may be included in the system environment 100. The embodiments described herein can be adapted to other suitable online systems that manage medications for users.

The client devices 120 are one or more computing devices capable of receiving user input as well as transmitting and/or receiving data via the network 110. In one embodiment, a client device 120 is a conventional computer system, such as a desktop or a laptop computer. Alternatively, a client device 120 may be a device having computer functionality, such as a personal digital assistant (PDA), a mobile telephone, a smartphone or another suitable device. A client device 120 is configured to communicate via the network 110. In one embodiment, a client device 120 executes an application allowing a user of the client device 120 to interact with the medication management system 130 as either a user of an application to access medication information or a reviewer using a review tool to review batches in a review queue associated with medication information of users of the medication management system 130. For example, the user can use an application that allows the user to use a camera integrated into the client device 120 and allows the user to import images or videos into the application. A user of an application to access medication information can use a first client device referred to as 120A and a reviewer using a review tool to review batches in a review queue can use a second client device referred to as 120B hereon. For example, a client device 120 executes a browser application to enable interaction between the client device 120 and the medication management system 130 via the network 110. In another embodiment, a client device 120 interacts with the medication management system 130 through an application programming interface (API) running on a native operating system of the client device 120, such as IOS® or ANDROID™.

The client devices 120 are configured to communicate via the network 110, which may comprise any combination of local area and/or wide area networks, using both wired and/or wireless communication systems. In one embodiment, the network 110 uses standard communications technologies and/or protocols. For example, the network 110 includes communication links using technologies such as Ethernet, 802.11, worldwide interoperability for microwave access (WiMAX), 3G, 4G, code division multiple access (CDMA), digital subscriber line (DSL), etc. Examples of networking protocols used for communicating via the network 110 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over the network 110 may be represented using any suitable format, such as hypertext markup language (HTML) or extensible markup language (XML). In some embodiments, all or some of the communication links of the network 110 may be encrypted using any suitable technique or techniques.

One or more third party systems 140 may be coupled to the network 110 for communicating with the medication management system 130, which is further described below in conjunction with FIG. 2. In one embodiment, a third party system 140 is an application provider communicating information in databases or keys for accessing information in databases by a client device 120B. A third party system 140 may also communicate information in databases or keys for accessing information in databases to the medication management system 130.

Figure 2:
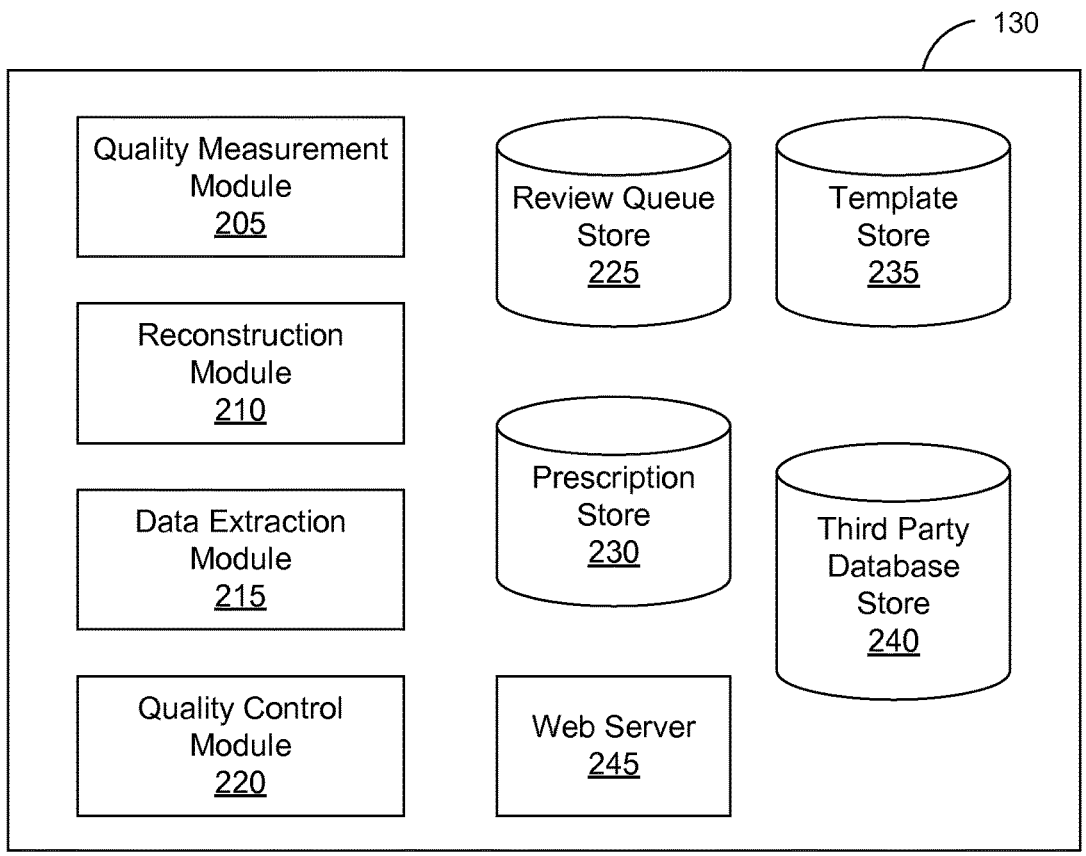
FIG. 2 is a block diagram of a medication management system, in accordance with an embodiment.

FIG. 2 is a block diagram of an architecture of the medication management system 130. The medication management system 130 shown in FIG. 2 includes a quality measurement module 205, a reconstruction module 210, a data extraction module 215, a quality control module 220, a review queue store 225, a prescription store 230, a template store 235, a third-party database store 240, and a web server 245. In other embodiments, the medication management system 130 may include additional, fewer, or different components for various applications. Conventional components such as network interfaces, security functions, load balancers, failover servers, management and network operations consoles, and the like are not shown so as to not obscure the details of the system architecture.

The quality measurement module 205 determines one or more quality measurements of an image where a quality measurement is associated with one or more adjustments in an image. An adjustment of an image can be a filter applied to an image or an adjustment of brightness, contrast, hue, saturation, color balance, one or more color vibrancies, levels, curves, exposure, thresholds, luminance, and any other suitable adjustment that can be made to an image. The quality measurement module 205 determines one or more quality measurements of an image and, based on the quality measurements, provides information describing the quality measurements to a user of the system 130. The provided information can include suggestions, instructions, or guidelines for improving quality of the images based on the quality measurements, as described further below in conjunction with FIGS. 3, 4A, and 4B.

The reconstruction module 210 accesses images of a medication label (may also be referred to as a label hereon) on a medication package (may also be referred to as a package hereon) where each image is associated with a portion of the label and determines structural information of a package where a portion of the label associated with an image is attached. Example medication packages include a prescription package, such as a pill bottle, medication box or tube, a liquid medication bottle, or other holder of medications. From here on, the medication in a medication package may also be referred to as content of the package. Based on the structural information, the reconstruction module 210 determines transform matrices for mapping a pixel of the portion of the label to a corresponding pixel on a flat surface. For example, the structural information can include an identification of an object similar in shape with the package and the transform matrices can be for mapping a pixel of the portion of the label on the object to a corresponding pixel on a flat surface. In other embodiments, the structural information can be a geometric model of the package or of a portion of the package where the label is attached or a point cloud representation of the package or of a portion of the package where the label is attached. Overlapping features are determined in each of the images in a set of images where an overlapping feature in a first image in the set of images is also in a second image in the set of images. Then, the reconstruction module 210 reconstructs the label on the package using a set of images capturing portions of the label, the overlapping features in the images in the set of images, and the transform matrices, as further described below in conjunction with FIG. 5.

The data extraction module 215 identifies or extracts machine-readable information or text in an image or a reconstructed label using one or more text recognition algorithms, one or more object recognition algorithms, or any other suitable feature recognition algorithm. Associations are determined between the identified text and one or more types of information where a type of information can be information about content in the package or information about the user. In one embodiment, the data extraction module 215 determines these associations based on a determination of a template that matches the reconstructed label. For example, if the template is known to have a certain type of information in a first slot in an upper right corner of a label, then the identified text in the upper right corner of the reconstructed label is associated with the certain type of information. The identified text in a reconstructed label and determined associations of the identified text with one or more types of information is stored in the review queue store 225 as a batch which also includes a set of images used to reconstruct the reconstructed label. The function provided by the data extraction module 215 is further described below in conjunction with FIG. 5.

The quality control module 220 selects one or more batches in the review queue store 225 to duplicate in the review queue store 225 or provide to reviewers via a review tool executing on a client device 120B a plurality of times for quality control (QC). Thus, the system 130 can control for quality based on differences between reviews of the same batch and ensure a certain level of thoroughness when reviewing a reconstructed label, the identified text of the reconstructed label, and associations of the identified text with types of information when importing a structured prescription record based on the reconstructed label, identified text, and determined associations, as further described below in FIG. 5.

The review queue store 225 stores one or more review queues where each review queue includes one or more batches. As previously described, a batch includes a set of images capturing a label on a package, identified text of a reconstructed label reconstructed based on the set of images, and determined associations of the identified text and one or more types of information. A batch can also store a reconstructed label associated with the set of images. For batches in the review queue that have been reviewed by a reviewer operating a client device 120B, the batch can also be associated with a structured prescription record confirmed by the reviewer.

The prescription store 230 stores structured prescription records of users of the medication management system 130. In one embodiment, the stored structured prescription records are stored in association with identifiers of users and, in another embodiment, the prescription store 230 stores one or more user profiles associated with users of the medication management system 130 and each user profile associated with a user includes structured prescription records associated with the user. The prescription store 230 can also store a batch associated with a user in the user's user profile or associated with an identifier of the user.

The template store 235 stores one or more templates and companies associated with the one or more templates. For example, if company A is known to use a first type of template for a label and a second type of template for a label, the template store 235 stores the first type of template, the second type of template, and an association with company A with the first and second types of templates. Thus, if Walgreens is known to use a certain type of template for prescription or medication labels, then the template store 235 can store the certain type of template in association with Walgreens. Each template in the template store 235 includes one or more slots and, for each slot in the template, stores a type of information associated with the slot. For example, if a first slot in a template is known to be associated with a first type of information (e.g., user name), then the template store 235 stores the first slot in the template in association with the first type of information. In one embodiment, a location of the first slot in the template is associated with the first type of information.

The third-party database store 240 stores information from one or more databases associated with third party systems 140 or keys accessing information in one or more databases associated with third party systems 140. For example, if a known drug company is company A, then the medication management system 130 may have access to company A's databases and company A may have access to the prescription store 230 of the medication management system 130. In one embodiment, information associated with a user of the system 130 included in a database in a third party system 130 is only accessible by the system 130 if the user gives permission for the information to be transferred.

The web server 245 links the medication management system 130 via the network 110 to the one or more client devices 120, as well as to the one or more third party systems 140. The web server 245 serves web pages, as well as other content, such as JAVA®, FLASH®, XML, and so forth. The web server 245 may receive and route messages between the medication management system 130 and the client device 120, for example, information describing quality measurements, reviewed batches, structured prescription records, or other suitable messages. Additionally, the web server 245 may provide application programming interface (API) functionality to send data directly to native client device operating systems, such as IOS®, ANDROID™, WEBOS® or BlackberryOS.

Preprocessing a Set of Images Using Quality Measurements

Figure 3:
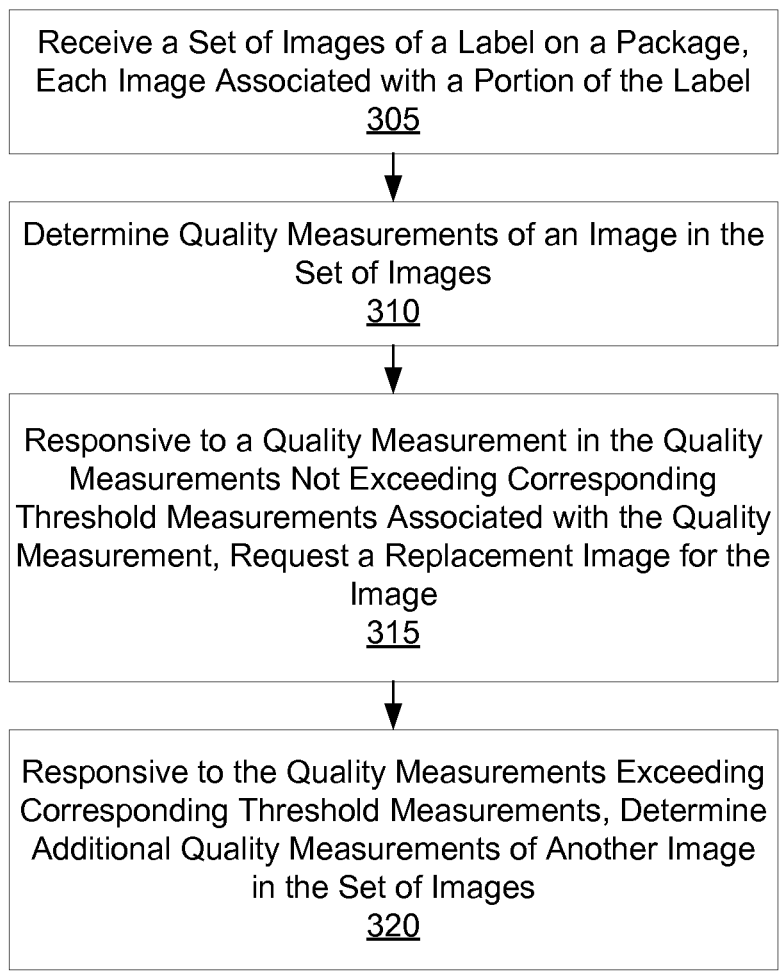
FIG. 3 is a flowchart of a method for preprocessing a set of images using quality measurements, in accordance with an embodiment.

FIG. 3 is a flowchart of a method for preprocessing a set of images using quality measurements. In various embodiments, the steps described in conjunction with FIG. 3 may be performed in different orders. Additionally, in some embodiments, the method may include different and/or additional steps than those shown in FIG. 3. The functionality described in conjunction with the medication management system 130 in FIG. 3 may be provided by the quality measurement module 205, in one embodiment, or may be provided by any other suitable component, or components, in other embodiments. Additionally, the client device 110 may execute one or more instructions associated with the medication management system 130, such as an application associated with the medication management system 130, to provide the functionality described in conjunction with FIG. 3.

The system 130 receives 305 a set of images of a label on a package (e.g., a prescription package, such as a pill bottle, medication box or tube, a liquid medication bottle, or other holder of medications) associated with a user from a client device operated by the user. Each image in the set of images is associated with a portion of the label. For example, each image captures a portion of the label and each image is associated with or captures a different portion of the label than other images in the set of images. Thus, if a first image in the set of images is associated with a top right corner of the label, then a second image in the set of images is associated with at least a portion of the label that is not the top right corner of the label. The label on the package can be any portion of the package including information about content in the package or information about the user. The information about content in the package can include information identifying the content, instructions for interacting with the content, an expiration date associated with the content, warnings for interacting with the content, and any other suitable helpful information about the content and safety of the user while interacting with the content. If the content includes pills, then interacting with the content includes consuming the pills. The information about the user can include the user's name, address, phone number, and any other suitable contact information associated with the user. In some embodiments, a single image is captured, such as one that is focused on what is determined to be a key part of the label or possibly a panoramic view image.

In alternative embodiments, the set of images can be a video feed and can be automatically captured by an application executing on the client device operated by the user that is associated with the system 130. For example, a video feed or images can be captured automatically based on camera motion (based on motion data from a motion sensor integrated in the client device 120), values associated with pixels in the image, any suitable real-time analysis of the images, information describing an environment where the image or video feed is being captured, or any combination thereof.

One or more quality measurements of an image in the set of images are determined 310. Each quality measurement is associated with one or more adjustments in the image. An adjustment of an image includes adjusting brightness, contrast, hue, saturation, color balance, one or more color vibrancies, levels, curves, exposure, thresholds, luminance, and any other suitable adjustment that can be made to an image. The adjustment of an image can also be a filter applied to the image. A quality measurement of an image is a measurement of an adjustment of the image. For example, if the adjustment of the image is contrast, then the quality measurement of the image can be a measurement of how much contrast has been adjusted for the image. Responsive to determining 310 one or more quality measurements of an image in the set of images, the system 130 can present information to the user describing the quality measurements, as further described below in conjunction with FIGS. 4A and 4B. Similarly, the system 130 can present to the user, via an application executing on a client device 120 operated by the user, instructions for rotating the package in a certain orientation, as further described below in conjunction with FIGS. 4A and 4B.

In response to a quality measurement (e.g., in the one or more quality measurements determined as described above) not exceeding one or more threshold measurements associated with one or more adjustments of the quality measurement, the system 130 requests 315 a replacement image for the image. In one embodiment, the one or more quality measurements are for lighting, camera motion, and focus. Thus, an application associated with the system 130 executing on the client device 120 checks for lighting, camera motion, and focus through luminance values in an image, motion data associated with the client device 120, and edge density analysis, respectively.

The application can check for sufficient lighting through the luminance values of the image. The application extracts the luminance values of the image and, if the captured image is in YUV format, the luminance values are simply the Y components of the pixel values. If the image is in another format, a color space transform can be applied to the image to convert the image into YUV format. The application or the server 130 can determine a histogram of the luminance values and determine brightness and a contrast of the image based on a minimum value associated with the histogram, a maximum value associated with the histogram, a difference between the minimum value and the maximum value, or any combination thereof. Responsive to brightness, contrast, or both brightness and contrast of the image not exceeding corresponding threshold measurements associated with brightness, contrast, or both brightness and contrast, respectively, the application can display information to the user describing the brightness and contrast of the image. For example, the information displayed can include a message encouraging the user to increase the ambient lighting, a message informing the user that more light is needed for accuracy, or any other suitable message assisting the user in capturing an image with better quality.

The application can check for camera motion via an accelerometer or any other suitable motion sensor integrated into the client device 120 operated by the user executing the application. For an accelerometer, if a magnitude of the accelerometer readings is above a threshold measurement associated with the accelerometer readings, the application can display information to the user describing the motion of the camera and whether the camera needs to be steadier during image capture.

The application or the system 130 can also check for focus by applying one or more filters to an image. For example, the application can apply a Gaussian blur filter to the image to eliminate spurious high-frequency artifacts, a Laplacian filter to detect edges, or any combination thereof. An edge density value associated with the image after the image is filtered can be determined. The edge density value can be an average edge density value for a plurality of sample points in the image, a maximum edge density value associated with the image, or any other suitable combination of edge density values in the image. If the edge density value does not exceed a threshold measurement associated with edge densities, the application can display information to the user describing edge density in the image. The threshold measurement for edge densities can be based on empirical testing on various device models and configurations.

The system 130 can determine one or more threshold measurements corresponding to one or more quality measurements measuring adjustment levels of an image. Thus, a quality measurement of an image exceeding a corresponding threshold measurement represents the image having an adjustment of the image that does not lessen the quality of the image. For example, if the quality measurement of an image is a measurement of contrast, then the quality measurement exceeding a corresponding threshold measurement associated with contrast represents the image having enough contrast that details in the image are recognizable, such as text in the image. In another embodiment, a quality measurement of an image not exceeding a corresponding threshold measurement represents the image having an adjustment of the image that does not lessen the quality of the image. For example, if the quality measurement of an image is a measurement of exposure, then the quality measurement not exceeding a corresponding threshold measurement associated with exposure represents the image not having too much exposure so that details in the image such as text are recognizable. Rather than or in addition to threshold measurements, the system 130 can determine ranges of measurements associated with adjustment levels of an image. Thus, a quality measurement of an image that is within the range of measurements represents the image having an adjustment of the image that is within a range that does not lessen the quality of the image. The system 130 can also present information to the user describing whether one or more of the quality measurements exceed corresponding threshold measurements, do not exceed corresponding threshold measurements, are within a range of measurements determined by the system 130, or any combination thereof, as further described below in conjunction with FIGS. 4A and 4B.

In response to the one or more quality measurements exceeding corresponding threshold measurements associated with adjustments for the quality measurements, the system 130 determines 320 one or more additional quality measurements of another image in the set of images. If each of the quality measurements exceed corresponding threshold measurements, do not exceed corresponding threshold measurements, are within a range of measurements determined by the system 130, or any combination thereof, then the quality of the image is suitable for identifying details and features in the image as further described below in conjunction with FIG. 5. The system 130 can also determine whether the whole label is captured by the set of images where each image in the set of images captures at least a portion of the label and the set of images capture at least the whole label. Where each image in the set of images has quality measurements exceeding corresponding threshold measurements, the set of images can be stored in the review queue store 235 and the set of images will be used to reconstruct the label as described further below in conjunction with FIG. 5.

Presenting Information Describing Quality Measurements

Figure 4A:
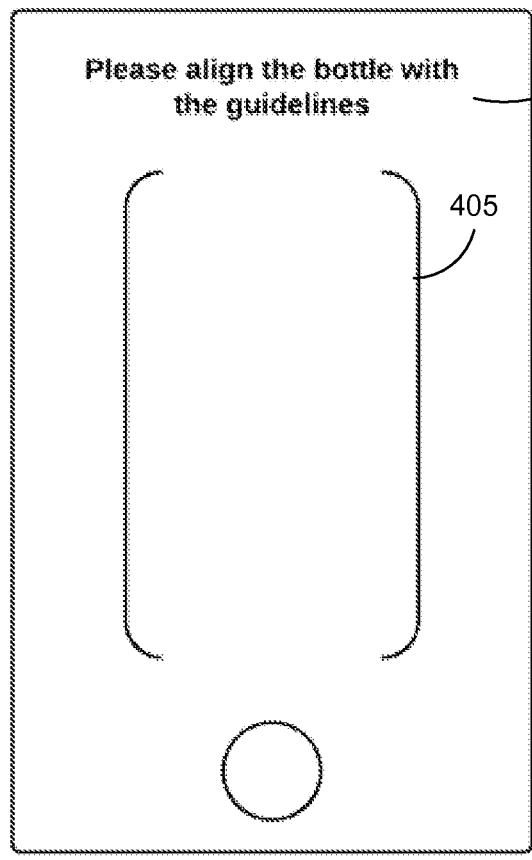
FIGS. 4A and 4B are examples of information presented to a user describing quality measurements, in accordance with an embodiment.
Figure 4B:
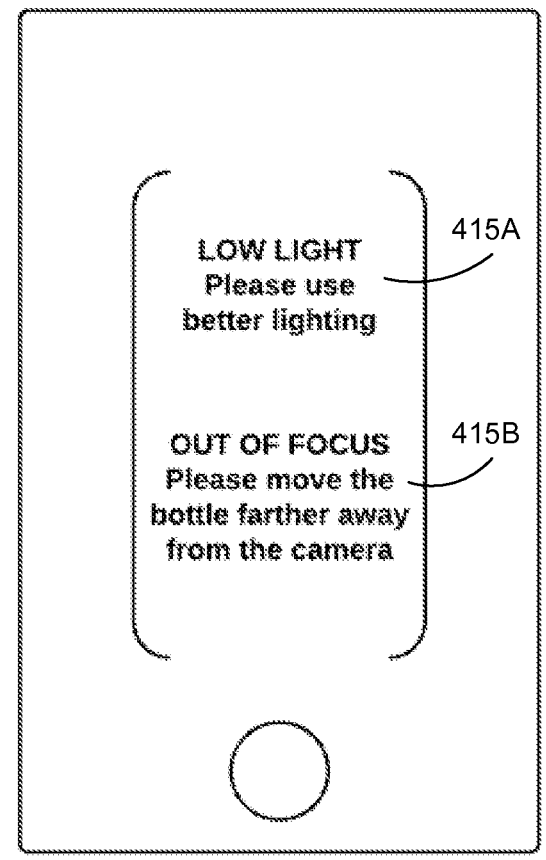

FIGS. 4A and 4B are examples of information presented to a user describing quality measurements. The system 130 can provide guidelines 405 to a client device 120 operated by a user for presentation to the user in an interface on an application executing on the client device 120, as shown in FIG. 4A. In addition to the guidelines 405, the system 130 can also present instructions 410 for presenting to the user such as "Please align the bottle with the guidelines." If the application was automatically capturing images responsive to rotation of a package such as the bottle, the instructions may also instruct the user to slowly rotate the package in a specific direction. Additional examples of instructions include "do not block the label," "take multiple pictures," "frame and focus the medication package," and "capture all the details," which can also be presented to the user via a client device 120 operated by the user prior to capturing images.

As shown in FIG. 4B, the system 130 can also provide information 415 describing quality measurements associated with a captured image or a real-time video feed. The information can describe whether quality measurement of an adjustment in a captured image or real-time video feed is above or below a threshold measurement associated with the adjustment. Thus, if the lighting is poor based on luminance values in an image not exceeding threshold luminance values, the information 415A can state "LOW LIGHT— Please use better lighting." If the focus is poor based on motion data of the client device 120 or edge density values associated with an image exceeding threshold measurements associated with motion data or threshold measurements associated with edge density values, respectively, the information 415B can state "OUT OF FOCUS—Please move the bottle farther away from the camera."

Reconstructing a Label and Extracting Information from the Label

Figure 5:
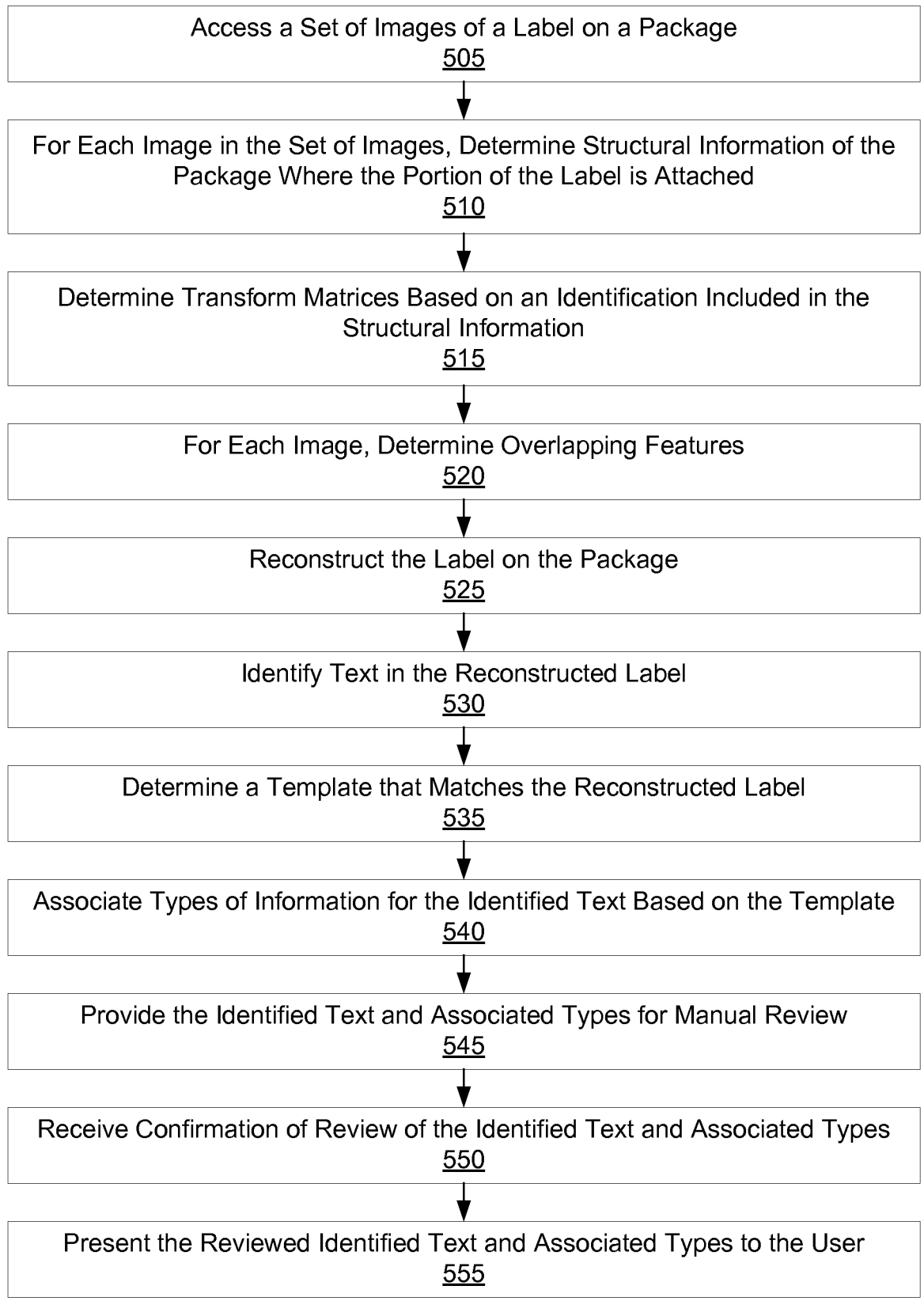
FIG. 5 is a flowchart of a method for reconstructing a label using a set of images and extracting information from the label, in accordance with an embodiment.

FIG. 5 is a flowchart of a method for reconstructing a label using a set of images and extracting information from the label. In various embodiments, the steps described in conjunction with FIG. 5 may be performed in different orders. Additionally, in some embodiments, the method may include different and/or additional steps than those shown in FIG. 5. The functionality described in conjunction with the medication management system 130 in FIG. 5 may be provided by the quality measurement module 205, the reconstruction module 210, and the data extraction module 215, or may be provided by any other suitable component, or components, in other embodiments. Additionally, the client device 120 may execute one or more instructions associated with the medication management system 130, such as an application associated with the medication management system 130, to provide the functionality described in conjunction with FIG. 5.

The system 130 accesses 505 a set of images of a label on a package. Each image in the set of images is associated with a portion of the label. The accessed set of images can be the set of images received 305 from the method described in conjunction with FIG. 3. The set of images can be stored in the review queue store 225 to help during a review process, as further described below. As previously described in conjunction with FIG. 3, one or more quality measurements associated with each image in the set of images can be determined 310 and compared to threshold measurements to determine whether a new image is needed.

For each image in the set of images, the system 130 determines 510 structural information of the package where the portion of the label associated with the image is attached or associated and determines 515 one or more transform matrices based on the structural information of the package for mapping a pixel of the portion of the label to a corresponding pixel on a flat surface. In one embodiment, the system 130 first identifies a location in each image in the set of images that is associated with a portion of the label associated with the image. For example, the location in an image associated with a portion of the label is identified based on assumptions known about the label. The assumptions can be a text color, background color, orientation of a label. For example, the assumptions can be that a label will have black text on a white background and be in a horizontal or vertical position on the image. Thus, using contrast, the system 130 can identify the location in an image associated with a portion of the label.

Structural information of the package where the portion of the label associated with the image is attached includes identification of a shape of the package, an identification of a shape of an object similar to the package, one or more identifications of shapes similar to the package, scores associated with one or more identifications of shapes similar to the package, and any combination thereof. Then, the system 130 determines 515 one or more transform matrices based on an identification included in the structural information. The structural information of the package can also include scores for one or more of the identifications where each score can be a weight or a percentage representing how similar a shape associated with the identification is to the package. Then, the system 130 determines 515 one or more transform functions based on the identification included in the structural information associated with the highest score or a score exceeding a threshold score. In one embodiment, a transform function can be a transform matrix where a transform matrix is an array or rectangular array of elements used to transform a point in a first space to a point in a second space. Thus, a pixel in the image where the portion of the label associated with the image is attached to the package is treated as a point in a first space defined by the structural information of the package where the label is attached. Thus, using a transform matrix, the system 130 maps the pixel to a corresponding pixel, which is a point in a second space that is a flat surface. The one or more transform matrices include any suitable transform matrix or transformation that removes perspective distortion, of the label on the package captured by the images in the set of images. Alternatively, the transform functions can be a model representing the package based on the structural information. For example, the model is a mathematical representation of the package based on the structural information such as an identification of a shape of the package. Thus, if the package is cylindrical in shape, then the model is a mathematical representation of a cylinder or cylindrical object.

Structural information of the package can also be a geometric model of the package or the portion of the label on the package. For example, the geometric model can be a point cloud representation or any other suitable 3D model of the package or the portion of the label on the package. Structural information can also include angles associated with the package. For example, if the package is tilted upwards, then the structural information can include a probable angle of the upward tilt.

One or more overlapping features in each of the images in the set of images are determined 520. An overlapping feature in an image in the set of images is a feature in the image corresponding to a second overlapping feature in another image in the set of images. For example, the label on the package may include borders that are straight lines and an overlapping feature can be a set of pixels in the border that appear in a portion of the label in an image in the set of images and in a portion of the label in another image in the set of images. In other examples, an overlapping feature can be a set of pixels or a set of pixels in a pattern that appear in a portion of the label in an image in the set of images and in a portion of the label in another image in the set of images. One or more overlapping features are determined 520 for each image in the set of images. Therefore, at least each image in the set of images has one or more overlapping features with another image in the set of images.

The system 130 reconstructs 525 the label on the package using the set of images, the one or more overlapping features in each of the images in the set of images, the one or more transform matrices, or any combination thereof. In one embodiment, the system 130 uses the one or more transform matrices to flatten each portion of the label in the images in the set of images and reconstructs 525 the label using the determined 520 one or more overlapping features in the images in the set of images. Alternatively, the system 130 uses the determined 520 one or more overlapping features in the images in the set of images to reconstruct 525 the label and flattens the reconstructed label using the one or more transform matrices. The label can be reconstructed 525 by stitching the images in the set of images together based on the overlapping portions in the images. Based on the one or more transform matrices, the system 130 maps pixels in the portion of the label in each image in the set of images to corresponding pixels in a second space of the reconstructed label. Each pixel in a portion of the label is associated with a transform matrix in the one or more transform matrices and the association can be based on the structural information. If the system 130 determines 510 that the package where a portion of the label is attached in a first image is a cylinder and that the package where a portion of the label is attached in a second image is a flat surface (such as the top or bottom of a pill bottle), the system 130 associates one or more of the pixels in the portion of the label in the second image with at least a transform matrix associated with a flat surface and associates one or more of the pixels in the portion of the label in the first image with at least a transform matrix associated with a cylinder. The one or more overlapping features in each of the images can be determined 520 after the system 130 reconstructs 525 the label as well.

Text in the reconstructed label is identified 530 using text recognition algorithms. In addition to text, the system 130 can identify 530 other features in the reconstructed label such as a barcode, a QR code, or any other suitable machine-readable representation of data. For identifying text, the system 130 can use optical character recognition, optical word recognition, intelligent character recognition, intelligent word recognition, or any other suitable text recognition algorithm.

The system 130 determines 535 a template that matches the reconstructed label. In one embodiment, the template is determined 535 based on the identified text. If the identified text includes a name of a company, then the system 130 determines 535 that the reconstructed label uses a template that the company is known to use. As an example, if CVS is known to use a certain type of template and the identified text includes the sequence of characters "CVS," then the system 130 determines 535 that the reconstructed label uses the certain type of template. Alternatively, the template is determined 535 based on user profile information associated with the user. If the user profile information includes information stating a company from which the user purchases the content in the package such as medicine, the system 130 determines 535 the reconstructed label may be a template used by the company. However, the system 130 may determine 535 that the template used by the company is not the template of the reconstructed label based on associating 540 one or more types of information for the identified text, as described further below in the next step. Each template is associated with one or more slots of the template associated with a type of information. For example, a template associated with a company and, based on the association with the company, various slots in the template are associated with a type of information provided in the label. For example, a template can include a slot that is a designated sub portion of the label for a type of information such as information about content in the package or information about the user, as previously described in conjunction with FIG. 4. The template can be a template stored in the template store 235.

The system 130 associates 540 one or more types of information for the identified text in the reconstructed label. In one embodiment, the one or more types of information for the identified text are identified 540 based on a template associated with the reconstructed label. If the label is associated with a first company that is known to use a template including a slot in the upper left that is for the user's name, then the system 130 can associate identified text in the upper left of the reconstructed label as the user's name. In alternative embodiments, the system 130 associates 540 one or more types of information for the identified text in the reconstructed label based on the identified text. Based on patterns of characters in the identified text, the system 130 can associate 540 various patterns of the characters in the identified text with types of information. For example, if the characters include five numbers, then the system 130 can associate the five numbers with a zip code. If the characters include ten numbers, the system 130 can associate 540 the ten numbers as a phone number.

The system 130 provides 545 the identified text and associated one or more types of information for manual review by storing the identified text and associated one or more types of information in a review queue. Prior to providing 545 the identified text and associated one or more types of information for manual review, the system 130 can provide the identified text and associated one or more types of information to the user. For example, if the system 130 identifies 530 text in the reconstructed label and has not associated one or more types of information with the identified text, the system 130 can provide the identified text to the user for the user to associate with one or more types of information. If the system 130 has only associated one or more types of information for part of the text in the reconstructed label, then the system 130 can provide the identified text, the associated one or more types of information for part of the text, or any combination thereof to the user for the user to confirm the associations, associate 540 one or more types of information for the identified text, or both. The identified text and associated types of information are stored in a review queue in the review queue store 225. A review process for reviewing the review queue is further described below.

Confirmation of review of the identified text and associated one or more types of information is received 550. The received 550 confirmation can be a notification that the identified text and the reviewed one or more types of information associated with the identified text are stored and/or available for the user to access or that the identified text and reviewed one or more types of information are stored as a structured prescription record. The reviewed identified text and associated one or more types of information are presented 555 to the user and can be automatically presented 555 responsive to receipt 550 of the confirmation and as a structured prescription record. The identified text and associated one or more types of information can be presented 555 to the user as editable and selectable options so that, if the user identifies an error, the user can edit the identified text and/or the associations by easily selecting parts of the identified text and corresponding types of information. Thus, if the user sees that a portion of the phone number has been associated as a zip code, the user can easily select the zip code and an option associating the zip code as part of the phone number via options presented to the user responsive to the user selecting the zip code.

Review Process

As described previously, the server 130 provides 545 the identified text and associated one or more types of information for manual review by storing the identified text and associated one or more types of information in a review queue. Thus, the review queue includes one or more batches and each batch includes the set of images, identified text in a reconstructed label using the set of images, and associated one or more types of information for the identified text.

The batches in the review queue are presented to reviewers (e.g., users associated with the medication management system 130 or a pharmaceutical company) based on a dynamic queueing algorithm that optimizes for one or more objectives that can be specified in the server 130. An objective describes overall customer service quality such as how or when the user should receive the reviewed identified text. Examples of objectives include minimizing turnaround time from when a user takes images from the set of images to when the server 130 presents 555 the reviewed identified text and associated one or more types of information to the user, quality, quantity, and other suitable goals for delivering the reviewed information. An objective of quality means that the turnaround time may be longer but more people will receive thoroughly reviewed identified text and an objective of quantity means that the turnaround time may be shorter for more users of the server 130. Thus, the queuing algorithm determines an order of the batches in the review queue based on the objective. In one example, a maximum turnaround time and a minimum turnaround time associated with the review queue are compared to a threshold minimum turnaround time and a threshold maximum turnaround time. In one embodiment, if the minimum turnaround time is greater than the threshold minimum turnaround time, the queuing algorithm directs a reviewer to review the newest batch in the review queue to lower the overall minimum turnaround time associated with the review queue. If the maximum turnaround time is greater than the threshold maximum turnaround time, then the queuing algorithm directs a reviewer to review the oldest batch in the review queue to lower the overall maximum turnaround time associated with the review queue. An objective can also be to present parts of the reviewed identified text as it is reviewed and, in that embodiment, the queuing algorithm can also determine an order of the identified text to review for each batch as well based on the objective.

Reviewers fix, double check, or confirm the identified text and the associations of the identified text with one or more types of information. If necessary, the reviewers can also determine associations between the identified text and the associations with one or more types of information. During this review process, the reviewers can use a review tool which includes databases, an interface for viewing the images in the set of images, and an interface for correcting or determining associations between identified text and one or more types of information. The databases can be databases of companies as well as personal databases, as previously described in conjunction with FIG. 2. For example, if the content in the package includes pills and the label is associated with a pharmaceutical company, then the review tool can include access to the pharmaceutical company's database of users and corresponding prescription.

Figure 7:
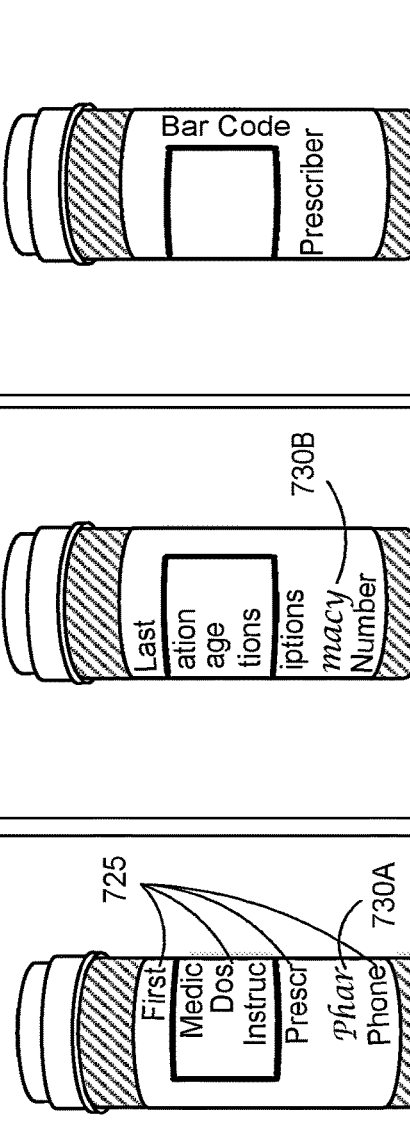
FIG. 7 is an example of a review tool used by a reviewer of the medication management system, in accordance with an embodiment.

A reviewer can review a batch in the review queue using a review tool, as described in conjunction with FIG. 7 which is an example of a review tool used by a reviewer of the medication management system 130. The review tool includes an interface for image presentation 705. The images can be presented in a horizontal format in the interface and the reviewer can have rotation capability of the images where each image captures or is of a portion of the prescription label on the medication package. As described previously in conjunction with FIGS. 2, 3, 4A, 4B, and 5, the portion of the prescription label includes text identifying first and last name, medication, dosage, instruction, prescription number, phone numbers, bar codes, refill dates, prescribers, and any other suitable information associated with the content in the medication package or information associated with the user, However, each image only captures a portion of the prescription label and, thus, each image may only capture a portion of the text as shown by the company name "Walgreens" in FIG. 7. The first image 720A captures a first portion 730A of the company name "Walgree" and the second image 720B captures a second portion 730B of the company name "reens" where the first portion 730A and second portion 730B overlap in at least the characters "ree." In addition, the first image 720A captures the first portion 730A and the text "Walgree" of the company name is distorted due to the curvature of the medication package or pill bottle. Similarly, the second image 720B captures the second portion 730B and the text "reens" of the company name is distorted due to the curvature of the medication package or pill bottle. Though blocked out for anonymity purposes, the rest of the text in the prescription label is also captured in various portions in various images 720A, 720B, and 720C distorted due to the curvature of the medication package as captured by the respective image in a similar manner as the example of the company name "Walgreens" and the captured portions 730A and 730B of the company name "Walgreens." The interface where the images are presented can also include fixed placement of rotation controls 710 for ease of multiple rotations where the rotation controls 710 are placed in a location that does not block the image. The reviewer can also zoom and freeze an image or a video. For example, a reviewer can select one or more images in a set of images included in a batch to zoom into. The review tool also includes an interface 715 for populating data fields. The interface can include previously auto-populated data fields based on identified text and compare the data fields with one or more databases, as previously described in conjunction with FIG. 2. Certain data fields can also be auto completed based on prescription numbers such as pharmacy or company names, store numbers, addresses, and phone numbers. The interface can also auto complete various data fields such as a date, a time, medication names, and dosages if acronyms or abbreviations were used instead. The review tool can also include various shortcuts that allow a reviewer using the review tool to quickly approve of the identified text and associated types of information. The review tool can also allow a reviewer to select a plurality of batches in the review queue that are all associated with the same user. Other suitable sort options for the batches are also included in the review tool such as sorting by timestamps (e.g., ordering the batches by when they were first stored in the review queue), sorting based on company name (e.g., to ease comparing identified text in a batch associated with images in the batch to a database associated with the company name), and any other suitable option to facilitate the review process to return thoroughly reviewed batches to users quickly.

As previously described in conjunction with FIG. 2, the review process can also include quality control (QC) process. The review process can include a plurality of tiers of reviewers where reviewers with more experience would be in a higher tier primarily reviewing conflicted reports from reviews by reviewers in a lower tier. For example, the system 130 can duplicate random batches in the review queue and have the same batch reviewed by a plurality of different reviewers. If there is a conflict in the reviews of the same batch, a reviewer in the higher tier would review the batch to resolve the conflict. In another embodiment, the system 130 can determine a conflict measurement in the reviews of the same batch and if the conflict measurement exceeds a threshold conflict measurement, then the batch is reviewed by a reviewer in the higher tier. For example, a conflict measurement can be a number of data fields that differ in the reviews, a number of characters that differ in the reviews, based on whether medication amount differs in the reviews, or any combination thereof.

Features Available to a User of the Medication Management System

A user of the medication management system 130 has access to various features associated with a stored prescription record, many of which can be automatically set up by the system based on the record without requiring additional user input (or requiring minimal user input or simply user confirmation of a feature) after the taking of the images of the medication label. Example features include content-based updates, network updates, and medication history and management options. A content-based update can be a feature that is specific to content in the package and assists with interaction with the content. A network update can be a feature specific to content in a package of another user that is in your network or care zone. Medication history and management options include other features that a user has based on the user's medication history, user profile information, or any other suitable information stored by the system 130 associated with the user. The various features will be described in conjunction with FIGS. 6A, 6B, 6C, 6D, 6E and 6C which are examples of a user interface of an application associated with the medication management system 130 used by a user of the medication management system 130.

Figure 6A:
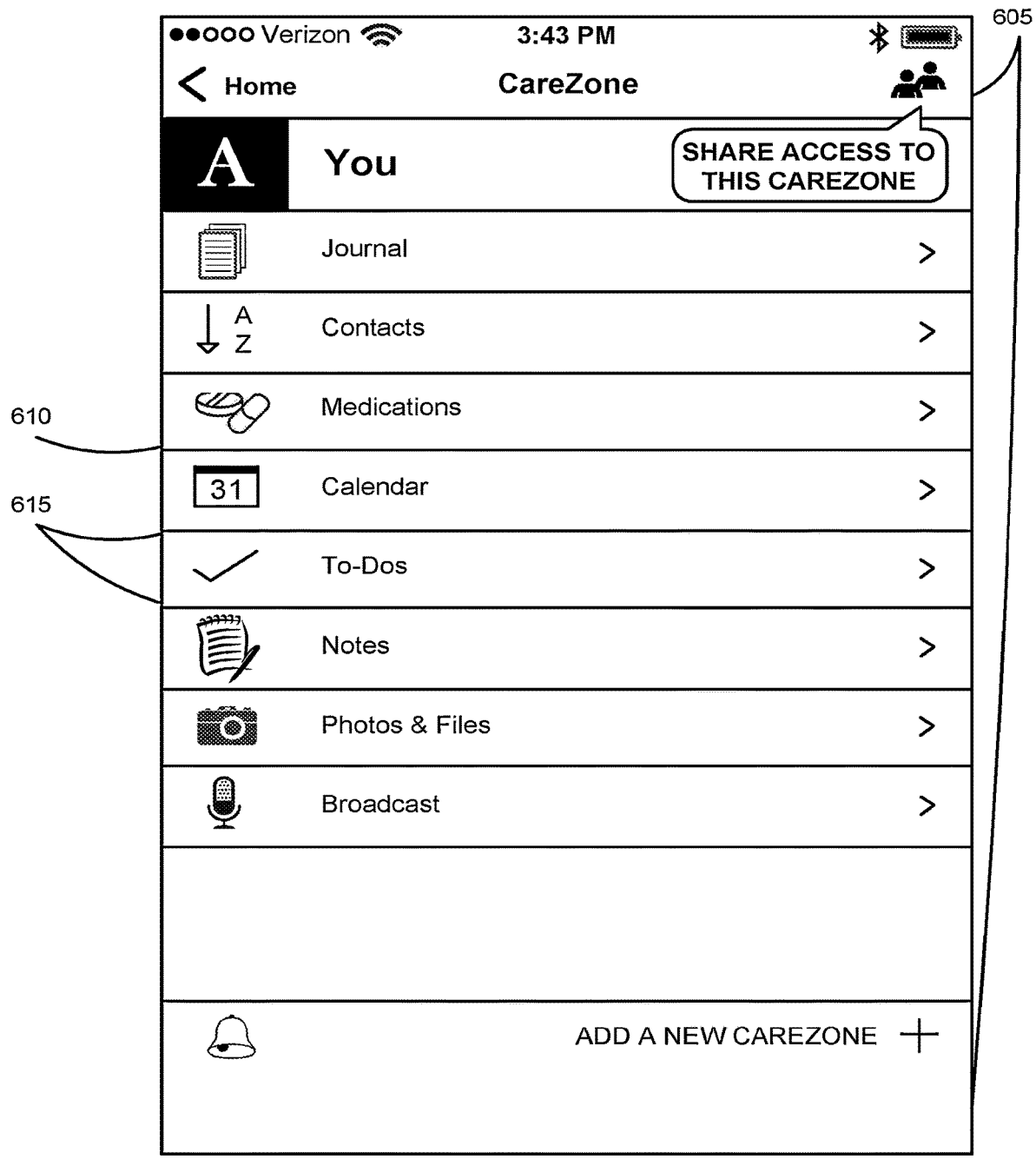
FIGS. 6A, 6B, 6C, 6D, 6E, and 6F are examples of a user interface of an application associated with the medication management system used by a user of the medication management system, in accordance with an embodiment.
Figure 6B:
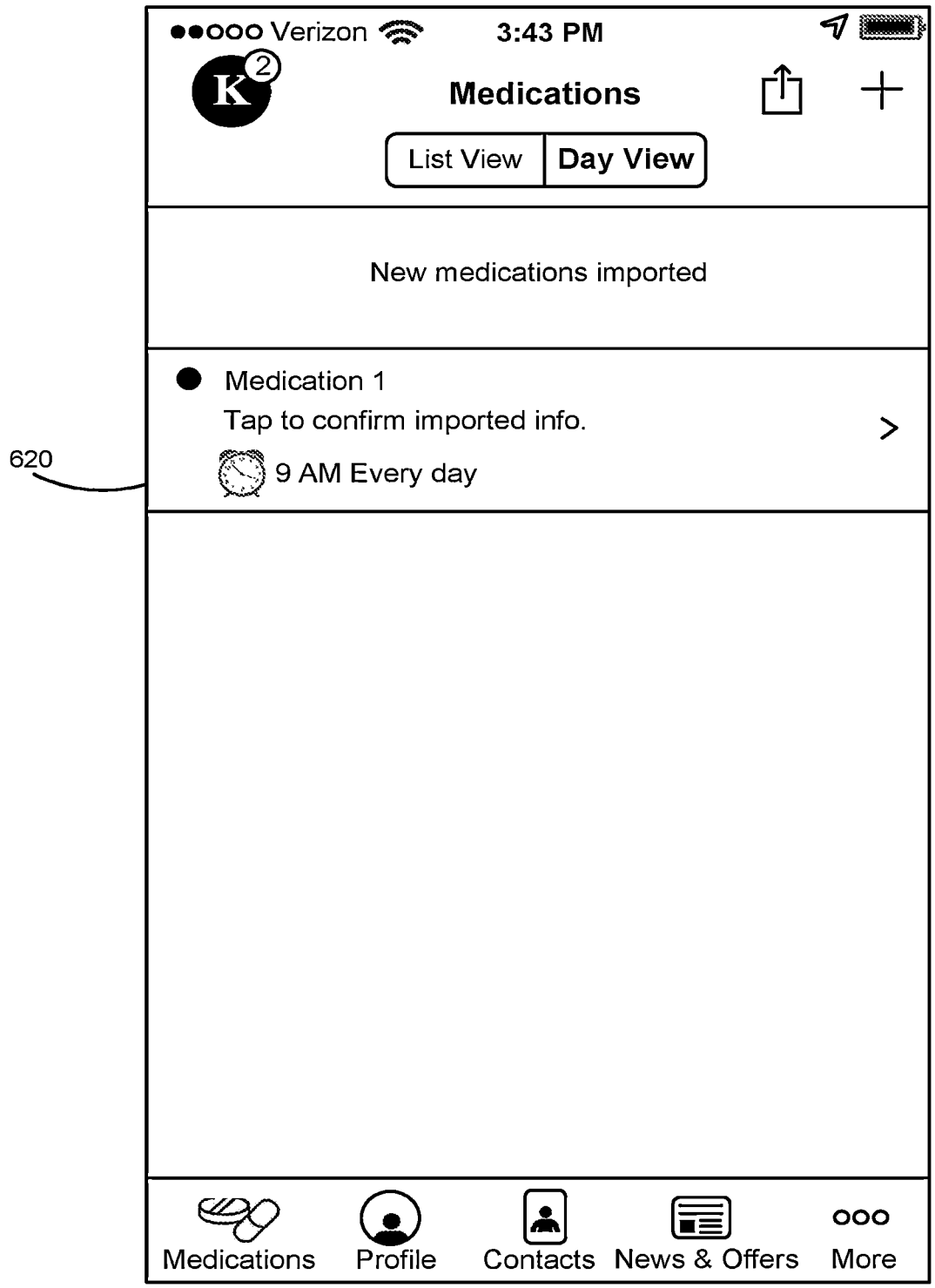
Figure 6C:
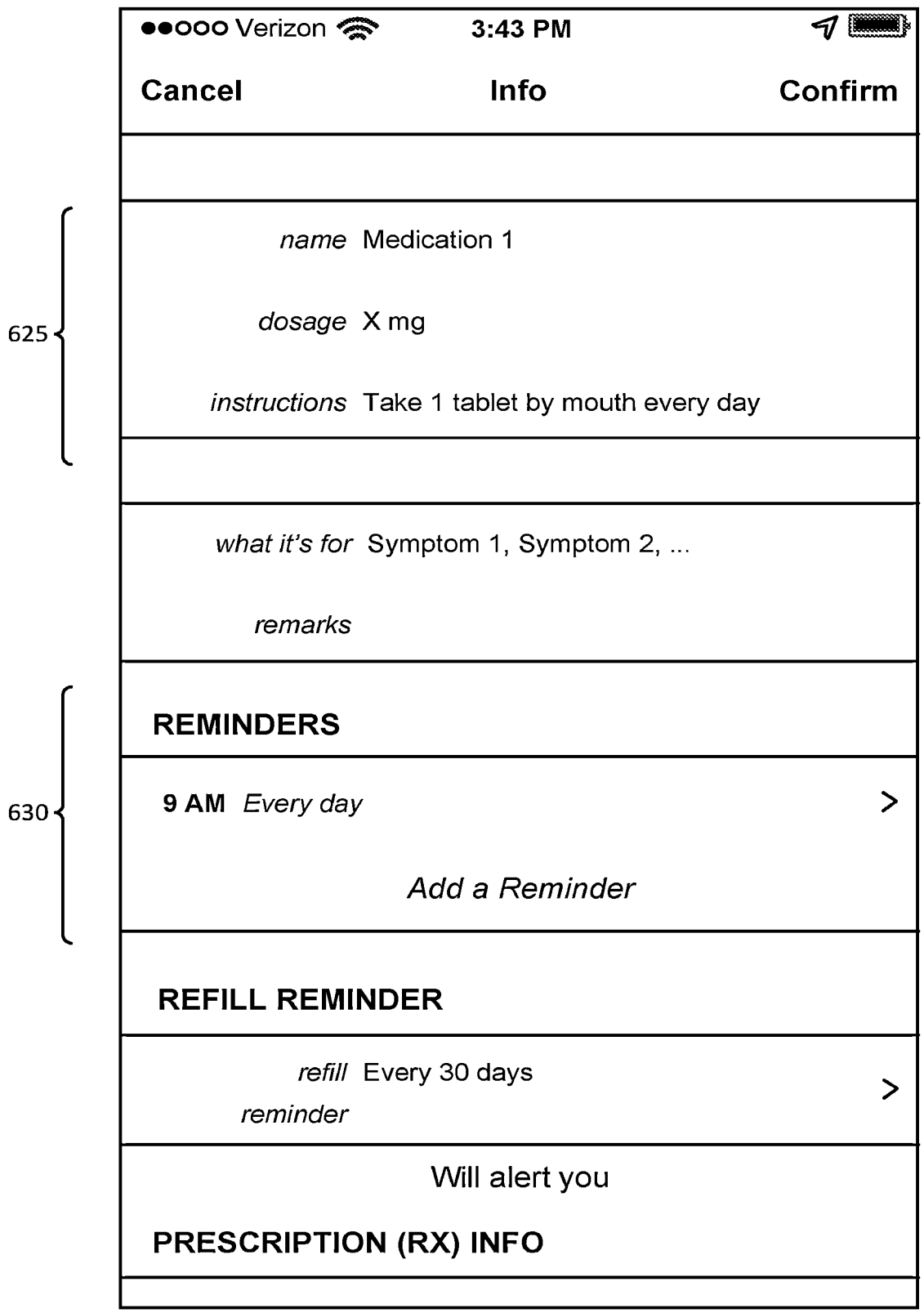
Figure 6D:
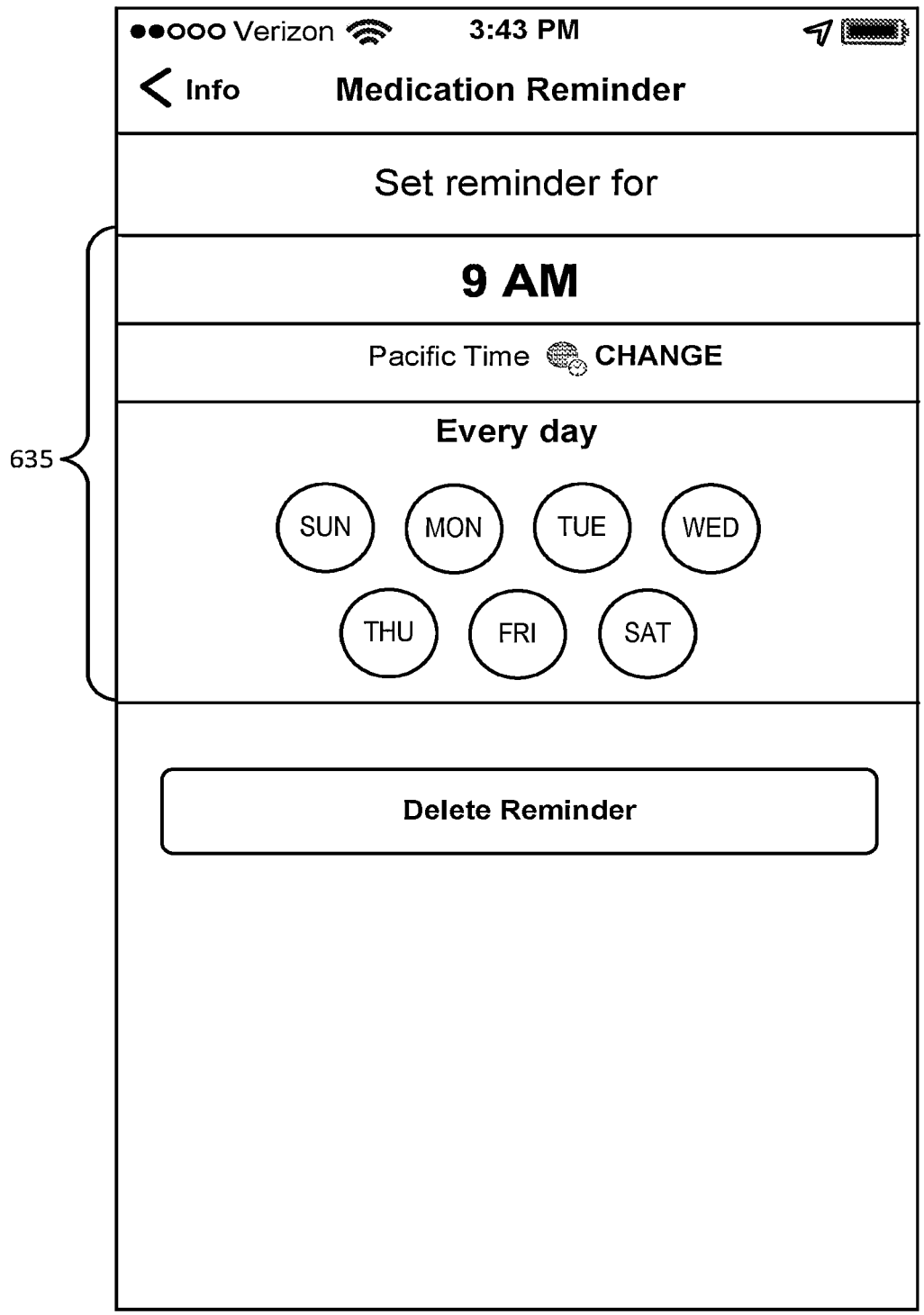
Figure 6E:
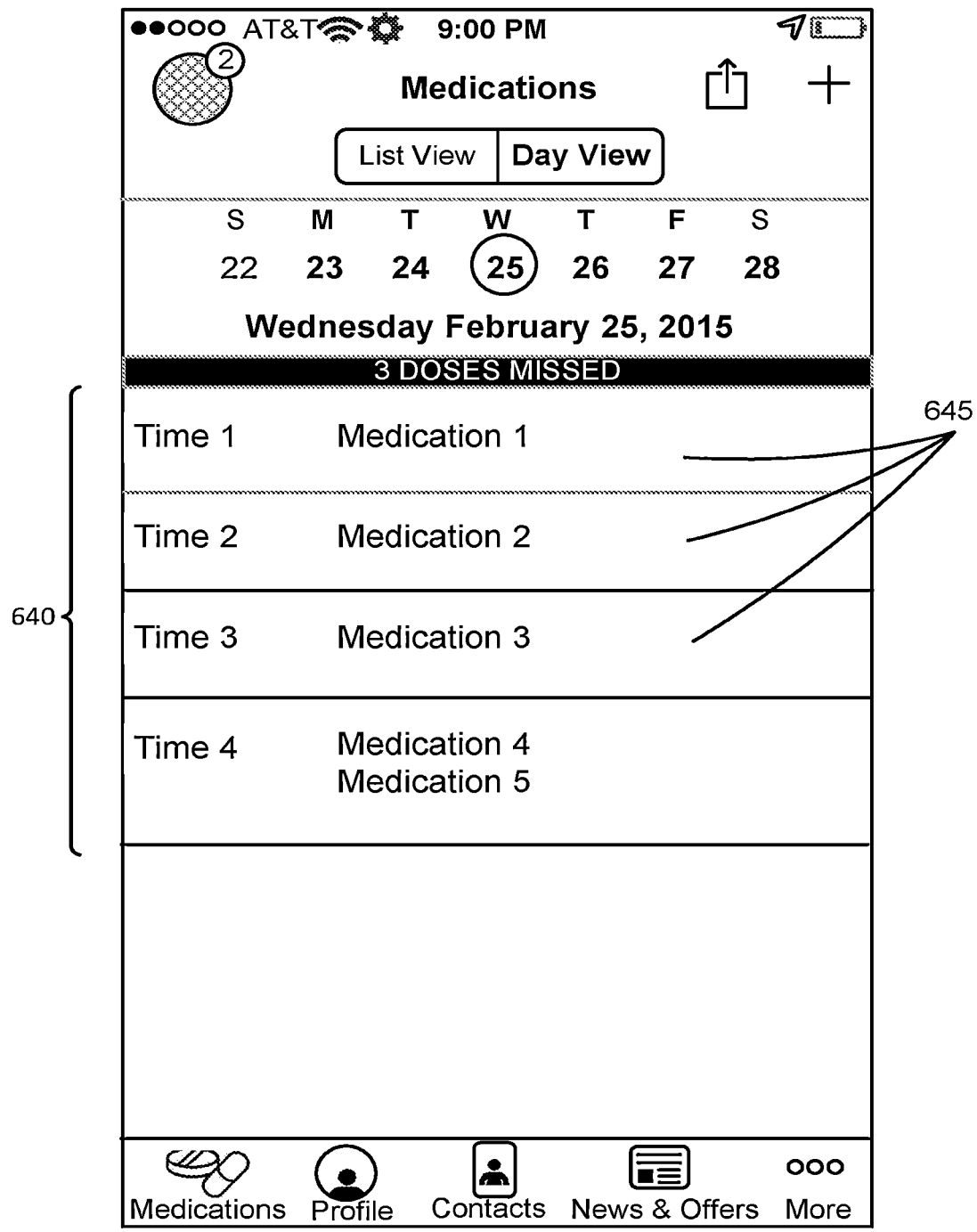
Figure 6F:
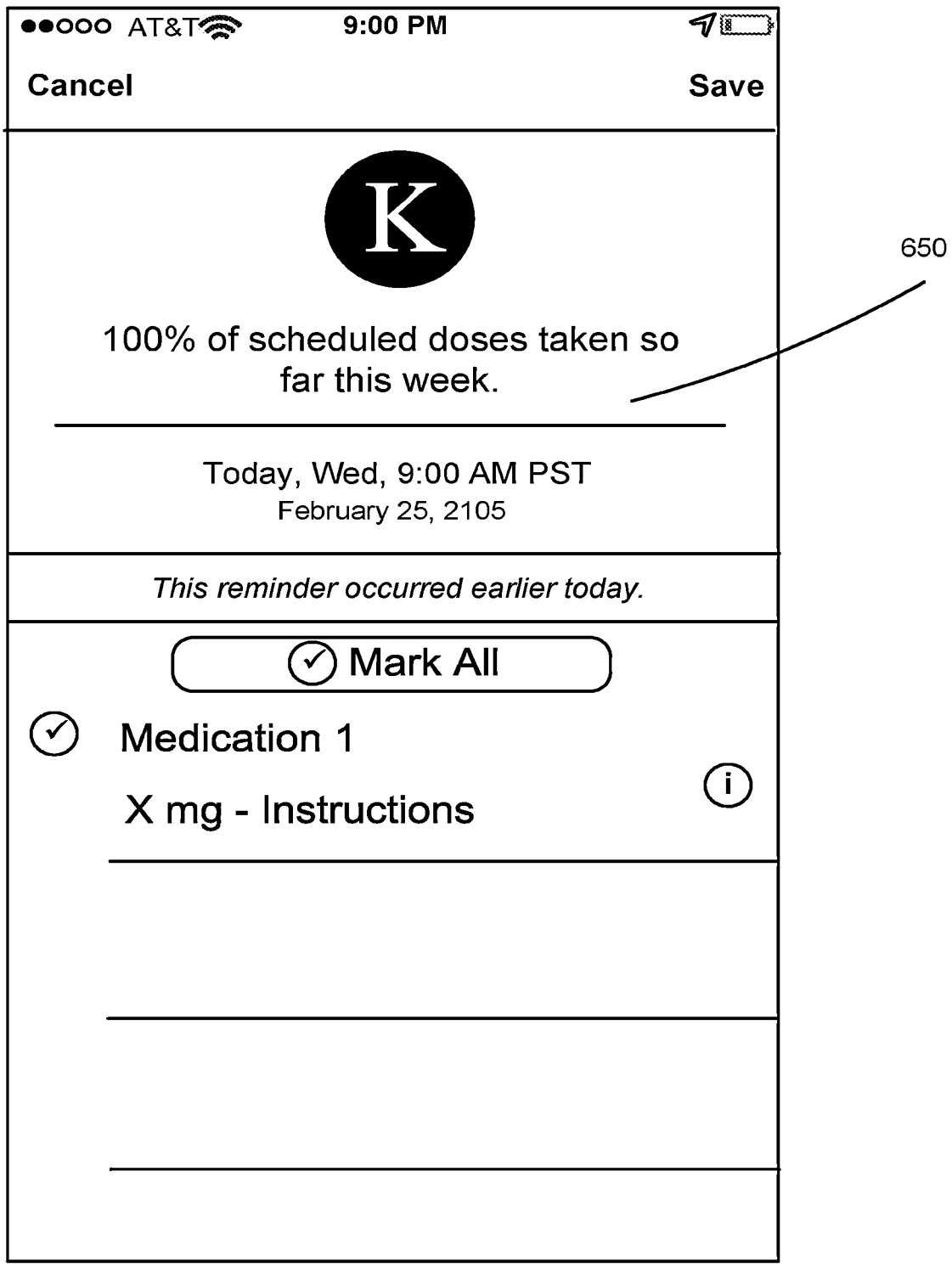

Content-based updates can include reminders based on structured prescription records associated with the user. Example reminders can be when to refill the prescription or content and when to take a next dosage and can be accessible by a user via a calendar 615 or a to-do list 615 in one embodiment, as shown in FIG. 6A. In addition, a reminder can be for notification that identified text and associations of the identified text with types of information have been reviewed and stored as a structured prescription record, as shown in 620 in FIG. 6B. For example, the structured prescription record can be "take 1 pill twice daily" and the two reminders can be created saying "take 1 pill" that are presented to the user twice a day. Reminders can also be customizable allowing for a user to accommodate for "as needed" instructions included in structured prescription records and an example interface for customizing reminders is shown in FIG. 6C. As shown in FIG. 6C, a user is presented with stored prescription record information 625 the prescription, dosage, and instructions and has options for creating reminders as seen in 630. If the instructions state no specific schedule but to "take as many as you want but not more than X in Y hours," the user can set up a plurality of reminders for every Y hours with a reminder to not take any if X dosages have already been taken. If the instructions state to "take a dosage at bedtime," the reminder can be "take a pill" at a default night time such as 9 PM and the user can change the default night time to when the user usually sleeps, as shown in 635 in FIG. 6D. The user can also be presented a list of daily medication reminders 640 as shown in FIG. 6E, indicating whether the user has taken his or her dosage or not via indicators 645 such as color (of text), symbols, or other suitable visual notifications. In addition, the user can be provided information 650 describing how many dosages were taken and how many dosages were missed, as shown in FIG. 6F. Similarly, when it comes time to refill a prescription, the user can receive a reminder telling him it is time to refill the prescription and possibly auto-placing the refill order at the pharmacy used for the last order.

The system 130 allows a user to share his or her records with other members in his or her network or care zone, for example via options 605 as shown in FIG. 6A. Thus, a network update is a feature that is associated with another member in the user's network or care zone or that informs a user in the network of another member in the network's actions. For example, a first user (e.g., a mother) may need to take prescription medicine but the first user may not be a user of the system 130. Then, the first user can allow a second user (e.g., a daughter of the mother) access to his or her records on the system 130 and the second user would get reminders for the first user. In another example, parents may monitor prescription intake of their child so the parents can both be in the child's network or care zone. Thus, if a first parent gave the child his or her dosage in the morning and left without telling the second parent, the first parent can update the second parent via a feature that notifies the second parent that the dosage was given. If a third-party device is used to check whether a user takes his or her medication, a network update can be a notification associated with the third-party device. For example, a third-party device can be a radio-frequency identification (RFID) tag on a prescription bottle, a weight detection on a prescription bottle, or a proximity detection sensor (e.g., integrated in a necklace) that detect when a pill has passed by within a certain proximity and a network update can be an indication from the third-party device that a prescription bottle was opened, a prescription bottle weighs a little less, a pill passed by in proximity, or any other suitable indication associated with using the third-party device.

Medication history and management options are also features available to a user of the system 130. The user can request or have access to a complete list of current medications taken by the user based on the user's history with the system 130 as seen in 610 in FIG. 6A. In some embodiments, a medication list of all medications for which a label image has been captured is automatically generated and updated as new medications are imaged. Another option can be for various states or medical states of a user to be tracked, such as glucose levels of the user. If the system 130 is associated with another application that tracks the various states, the system 130 can also suggest using another application to the user. For example, the system 130 can provide for presentation to the user a notification that states "seems like you need to track glucose levels based on your meds— we suggest using this app for tracking glucose levels." Further, another option available to the user is for analysis of the user's prescription history and suggestions based on the analysis or based on the content in the package. A suggestion based on analysis can include a statement such as "the use of prescription X, Y, and Z at the same time is common in patients diagnosed with A—we suggest B," where B can be "taking this other combination of prescription," "switching from X to C because it's a cheaper generic equivalent and has same effects," "switching from X to C because it's a cheaper generic equivalent for your insurance plan," and "not taking X with Z in time interval D since the side effects can be E, F, and G." The user also has options available to facilitate in refilling or ordering prescription. For example, the user can have the option to be provided the refills or orders in various packets associated with when a dosage should be taken or with what a dosage should be taken. The user can receive multiple packets with pills in them labeled "breakfast packet," "lunch packet," "take with food," or "bedtime packet." The user can also specify where and when the refills or orders should be dropped off and be able to track the refills or orders.

Any one or more of the feature described above can be automatically set up for the user based merely on the user having taken an image to capture prescription information. Thus, the user does not have to manually input information or even set up reminders as this information can be automatically done by the system. In one embodiment, the system 130 automatically sets up these refill reminders, dosage tracking, reminders to take medications, medication lists, etc. for the user based on the information captured based on the image of the label that resulted in the structured prescription record such that the user automatically starts receiving reminders/tracking or can access a medication list after capturing the image. In another embodiment, the system 130 automatically provides a prompt to the user to confirm to have these features set up or otherwise collects information/input needed from the user for setting up the reminders. In a further embodiment, the user provides preferences upon initially setting up an account (e.g., I would like refill reminders for all medications or certain medications, but not reminders to take medications throughout the day), and these preferences are applied in automatically setting up these features as images are taken of prescriptions.

SUMMARY

The foregoing description of the embodiments of the invention has been presented for the purpose of illustration;

it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A system comprising:
   one or more processors;
   one or more non-transitory computer-readable media storing computing instructions that, when executed on the one or more processors, cause the one or more processors to perform operations comprising:
   displaying, by a medication management system, one or more instructions on a user interface of a mobile device to instruct a user to capture each respective image in a set of images of respective different portions of a prescription label on a medication package;
   determining, using contrast, a location of each respective image in the set of images that is associated with the respective different portions of the prescription label on the medication package;
   reconstructing, using the set of images and one or more transform functions, each of the respective different portions of the prescription label on the medication package as a flattened reconstruction of the respective different portions of the prescription label; and
   providing, by the medication management system, for display on the user interface, a reconstructed prescription label based at least in part on the flattened reconstruction of the respective different portions of the prescription label.

2. The system of claim 1, wherein the operations further comprise:
   providing information for display on the user interface of the mobile device that describes a quality measurement to the user;
   providing for display on the user interface a request for a respective replacement image to replace each respective image having the quality measurement, wherein replacement images are requested until the quality measurement exceeds a second threshold measurement, and wherein the replacement images comprise the respective replacement image;
   determining, for each respective image in the set of images of the medication package, structural information identifying (i) an object similar in shape to the medication package captured in each respective image, and (ii) a non-planar surface of the medication package in each respective image; and
   upon identifying that the non-planar surface of the medication package exists, determining the one or more transform functions for the non-planar surface of the medication package based on the structural information of the medication package captured in each respective image, the one or more transform functions operable for flattening a different portion of the prescription label on the non-planar surface based on the object identified by the structural information, wherein the one or more transform functions map a first pixel on the different portion of the prescription label on the non-planar surface of the medication package to a second pixel on a first flat surface.

3. The system of claim 2, wherein:
   the quality measurement of one or more respective quality measurements measuring a focus of each respective image in the set of images is based on edge density analysis of each respective image; and
   providing information to the user further comprises providing an instruction to the user to move a camera into focus during image capture using the camera on the mobile device.

4. The system of claim 1, wherein the operations further comprise:
   measuring a motion of the mobile device operated by the user to capture each respective image based on motion data from a motion sensor of the mobile device, wherein the motion sensor comprises an accelerometer;
   during image capture by a camera, monitoring the motion of the camera via the accelerometer, using the medication management system; and displaying image recapture information on the user interface to the user describing the motion of the camera when a magnitude of movement indicated by the accelerometer exceeds a third threshold, wherein the image recapture information comprises instructions to correct the motion of the camera during recapture of a set of new images by the camera on the mobile device.

5. The system of claim 1, wherein:
an adjustment of one or more respective adjustments of an image of the set of images is selected from at least one of:
  a filter applied to the image, a brightness in the image, a contrast in the image, a hue associated with the image, a saturation of the image, a color balance in the image, one or more color vibrancies of the image, an exposure of the image, a luminance of the image, or any combination thereof.

6. The system of claim 1, wherein the operations further comprise:
identifying the location in each image in the set of images associated with a respective portion of the prescription label based on one or more assumptions of the prescription label, wherein the one or more assumptions of the prescription label comprise text color and background color; and
based on the one or more assumptions of the prescription label, assuming that the prescription label comprises black text on a white background in a horizontal or vertical position on each image.

7. The system of claim 1, wherein:
the prescription label on a non-planar surface of the medication package is a curved label that curves around at least a portion of the medication package, wherein each respective image in the set of images captures the respective different portions of the curved label, wherein the set of images collectively capture an entirety of the curved label, wherein the one or more transform functions flatten the curved label by mapping a plurality of pixels of the curved label to corresponding pixels on a first flat surface, and wherein images in the set of images are stitched together based on overlapping features to create a flattened reconstruction of the curved label.

8. The system of claim 1, wherein the operations further comprise:
identifying a respective location in each respective image in the set of images associated with a respective location on the prescription label on the medication package based on assumptions about the prescription label,
wherein determining the one or more transform functions further comprises determining one or more transform matrices representing an array of elements used to transform points in space, and
wherein each of a plurality of pixels in each respective image corresponding to the respective location on the prescription label represents respective points in a first space that are mapped using the one or more transform matrices to each of a plurality of corresponding pixels on a second flat surface that represent respective points in a second space.

9. The system of claim 1, wherein the operations further comprise:
detecting a template for a known prescription label type matches the reconstructed prescription label;
performing text recognition on the reconstructed prescription label to identify text about the user and a prescription represented by the prescription label;
populating each of a plurality of particular data fields of a prescription record with the respective text identified in the text recognition that represents a correct type of the text to fill in each of the particular data fields; and
automatically creating for the user, using an application on the mobile device, a plurality of medication management features, wherein at least one of the plurality of medication management features comprises a list of all medications of the user for which images have been taken, and wherein the list of all medications automatically updates as new images of prescription labels are captured by the user.

10. The system of claim 1, wherein the operations further comprise:
sharing, via an application on the mobile device, access to a prescription record of the user with a plurality of other client devices of other members within a network of the user, wherein each of the other client devices are configured to access a list of all medications of the user.

11. A method being implemented via execution of computing instructions configured to run on one or more processors and stored at one or more non-transitory media, the method comprising:
displaying, by a medication management system, one or more instructions on a user interface of a mobile device to instruct a user to capture each respective image in a set of images of respective different portions of a prescription label on a medication package;
determining, using contrast, a location of each respective image in the set of images that is associated with the respective different portions of the prescription label on the medication package;
reconstructing, using the set of images and one or more transform functions, each of the respective different portions of the prescription label on the medication package as a flattened reconstruction of the respective different portions of the prescription label; and
providing, by the medication management system, for display on the user interface, a reconstructed prescription label based at least in part on the flattened reconstruction of the respective different portions of the prescription label.

12. The method of claim 11 further comprising:
providing information for display on the user interface of the mobile device that describes a quality measurement to the user;
providing for display on the user interface a request for a respective replacement image to replace each respective image having the quality measurement, wherein replacement images are requested until the quality measurement exceeds a second threshold measurement, and wherein the replacement images comprise the respective replacement image;
determining, for each respective image in the set of images of the medication package, structural information identifying (i) an object similar in shape to the medication package captured in each respective image, and (ii) a non-planar surface of the medication package in each respective image; and
upon identifying that the non-planar surface of the medication package exists, determining the one or more transform functions for the non-planar surface of the medication package based on the structural information of the medication package captured in each respective image, the one or more transform functions operable for flattening a different portion of the prescription label on the non-planar surface based on the object identified by the structural information, wherein the one or more transform functions map a first pixel on the different portion of the prescription label on the non-planar surface of the medication package to a second pixel on a first flat surface.

13. The method of claim 12, wherein:
the quality measurement of one or more respective quality measurements measuring a focus of each respective image in the set of images is based on edge density analysis of each respective image; and
providing information to the user further comprises providing an instruction to the user to move a camera into focus during image capture using the camera on the mobile device.

14. The method of claim 11 further comprising:
measuring a motion of the mobile device operated by the user to capture each respective image based on motion data from a motion sensor of the mobile device, wherein the motion sensor comprises an accelerometer;
during image capture by a camera, monitoring the motion of the camera via the accelerometer, using the medication management system; and
displaying image recapture information on the user interface to the user describing the motion of the camera when a magnitude of movement indicated by the accelerometer exceeds a third threshold, wherein the image recapture information comprises instructions to correct the motion of the camera during recapture of a set of new images by the camera on the mobile device.

15. The method of claim 11, wherein:
an adjustment of one or more respective adjustments of an image of the set of images is selected from at least one of:
a filter applied to the image, a brightness in the image, a contrast in the image, a hue associated with the image, a saturation of the image, a color balance in the image, one or more color vibrancies of the image, an exposure of the image, a luminance of the image, or any combination thereof.

16. The method of claim 11 further comprising:
identifying the location in each image in the set of images associated with a respective portion of the prescription label based on one or more assumptions of the prescription label, wherein the one or more assumptions of the prescription label comprise text color and background color; and
based on the one or more assumptions of the prescription label, assuming that the prescription label comprises black text on a white background in a horizontal or vertical position on each image.

17. The method of claim 11, wherein:
the prescription label on a non-planar surface of the medication package is a curved label that curves around at least a portion of the medication package, wherein each respective image in the set of images captures the respective different portions of the curved label, wherein the set of images collectively capture an entirety of the curved label, wherein the one or more transform functions flatten the curved label by mapping a plurality of pixels of the curved label to corresponding pixels on a first flat surface, and wherein images in the set of images are stitched together based on overlapping features to create a flattened reconstruction of the curved label.

18. The method of claim 11 further comprising:
identifying a respective location in each respective image in the set of images associated with a respective location on the prescription label on the medication package based on assumptions about the prescription label,
wherein determining the one or more transform functions further comprises determining one or more transform matrices representing an array of elements used to transform points in space, and
wherein each of a plurality of pixels in each respective image corresponding to the respective location on the prescription label represents respective points in a first space that are mapped using the one or more transform matrices to each of a plurality of corresponding pixels on a second flat surface that represent respective points in a second space.

19. The method of claim 11 further comprising:
detecting a template for a known prescription label type matches the reconstructed prescription label;
performing text recognition on the reconstructed prescription label to identify text about the user and a prescription represented by the prescription label;
populating each of a plurality of particular data fields of a prescription record with the respective text identified in the text recognition that represents a correct type of the text to fill in each of the particular data fields; and
automatically creating for the user, using an application on the mobile device, a plurality of medication management features, wherein at least one of the plurality of medication management features comprises a list of all medications of the user for which images have been taken, and wherein the list of all medications automatically updates as new images of prescription labels are captured by the user.

20. The method of claim 11 further comprising:
sharing, via an application on the mobile device, access to a prescription record of the user with a plurality of other client devices of other members within a network of the user, wherein each of the other client devices are configured to access a list of all medications of the user.

* * * * *